United States Patent
Böcker et al.

(10) Patent No.: US 8,773,528 B2
(45) Date of Patent: Jul. 8, 2014

(54) REDUNDANT INSPECTION

(75) Inventors: Horst Böcker, Schwerte (DE); Heinrich Wiemer, Hamburg (DE)

(73) Assignee: KHS GmbH, Dortmund (DE)

( * ) Notice: Subject to any disclaimer, the term of this patent is extended or adjusted under 35 U.S.C. 154(b) by 470 days.

(21) Appl. No.: 12/995,110

(22) PCT Filed: May 29, 2009

(86) PCT No.: PCT/EP2009/003835
§ 371 (c)(1),
(2), (4) Date: May 27, 2011

(87) PCT Pub. No.: WO2009/156042
PCT Pub. Date: Dec. 30, 2009

(65) Prior Publication Data
US 2011/0216187 A1 Sep. 8, 2011

(30) Foreign Application Priority Data

Jun. 24, 2008 (DE) .......................... 10 2008 029 661

(51) Int. Cl.
*H04N 7/18* (2006.01)
*G01N 21/90* (2006.01)

(52) U.S. Cl.
CPC ............ *G01N 21/90* (2013.01); *G01N 21/9018* (2013.01); *G01N 21/9036* (2013.01)
USPC ....................................................... 348/127

(58) Field of Classification Search
CPC ....................... G01N 21/9036; G01N 21/9018
USPC ............................................. 348/127, 79, 80
See application file for complete search history.

(56) References Cited

U.S. PATENT DOCUMENTS

| | | | | |
|---|---|---|---|---|
| 3,105,907 A | * | 10/1963 | Colten et al. | 250/202 |
| 3,195,410 A | * | 7/1965 | Colten et al. | 409/96 |
| 5,910,844 A | * | 6/1999 | Phillips et al. | 356/614 |
| 6,122,048 A | * | 9/2000 | Cochran et al. | 356/239.4 |
| 6,172,748 B1 | | 1/2001 | Sones et al. | |
| 6,452,156 B2 | * | 9/2002 | Lindner | 250/223 B |
| 6,693,664 B2 | * | 2/2004 | Neumann | 348/126 |
| 8,389,893 B2 | * | 3/2013 | Kempe et al. | 219/121.72 |
| 2002/0126278 A1 | * | 9/2002 | Olshausen | 356/328 |
| 2006/0279821 A1 | * | 12/2006 | Riley et al. | 359/15 |
| 2008/0273086 A1 | * | 11/2008 | Sones et al. | 348/127 |
| 2008/0291438 A1 | * | 11/2008 | Akkerman et al. | 356/240.1 |
| 2010/0033811 A1 | * | 2/2010 | Westphal et al. | 359/368 |

(Continued)

FOREIGN PATENT DOCUMENTS

| | | |
|---|---|---|
| DE | 3611536 | 10/1987 |
| DE | 101 64 058 | 7/2002 |

(Continued)

*Primary Examiner* — Christopher S Kelley
*Assistant Examiner* — Asmamaw G Tarko
(74) *Attorney, Agent, or Firm* — Occhiuti & Rohlicek LLP

(57) ABSTRACT

The invention relates to an inspection device (1) for checking bottles (2) or similar containers, comprising at least one first camera (9, 11, 12, 13), which checks a defined region of the bottle (2) or similar container. The at least one camera (9, 11, 12, 13) is arranged on an optic channel (6), on which at least one second camera (9, 11, 12, 13) is arranged, which checks the same defined region as at least the first camera (9,11,12, 13). A third and fourth camera (9, 11, 12, 13) is arranged on the optical channel (6), which together check a further, defined region.

14 Claims, 1 Drawing Sheet

(56) References Cited

U.S. PATENT DOCUMENTS

| | | | |
|---|---|---|---|
| 2010/0097618 A1* | 4/2010 | Haisch et al. | 356/503 |
| 2010/0182418 A1* | 7/2010 | Jess et al. | 348/79 |
| 2011/0050884 A1* | 3/2011 | Niedermeier et al. | 348/127 |
| 2011/0164131 A1* | 7/2011 | Wiemer et al. | 348/127 |
| 2012/0154773 A1* | 6/2012 | Beyer | 355/52 |
| 2012/0235036 A1* | 9/2012 | Hatakeyama et al. | 250/310 |
| 2013/0100272 A1* | 4/2013 | Price et al. | 348/79 |

FOREIGN PATENT DOCUMENTS

| | | |
|---|---|---|
| DE | 102006034432 | 1/2008 |
| DE | 10 2006 047 150 | 4/2008 |
| WO | 2006/011803 | 2/2006 |
| WO | 2008/011960 | 1/2008 |

* cited by examiner

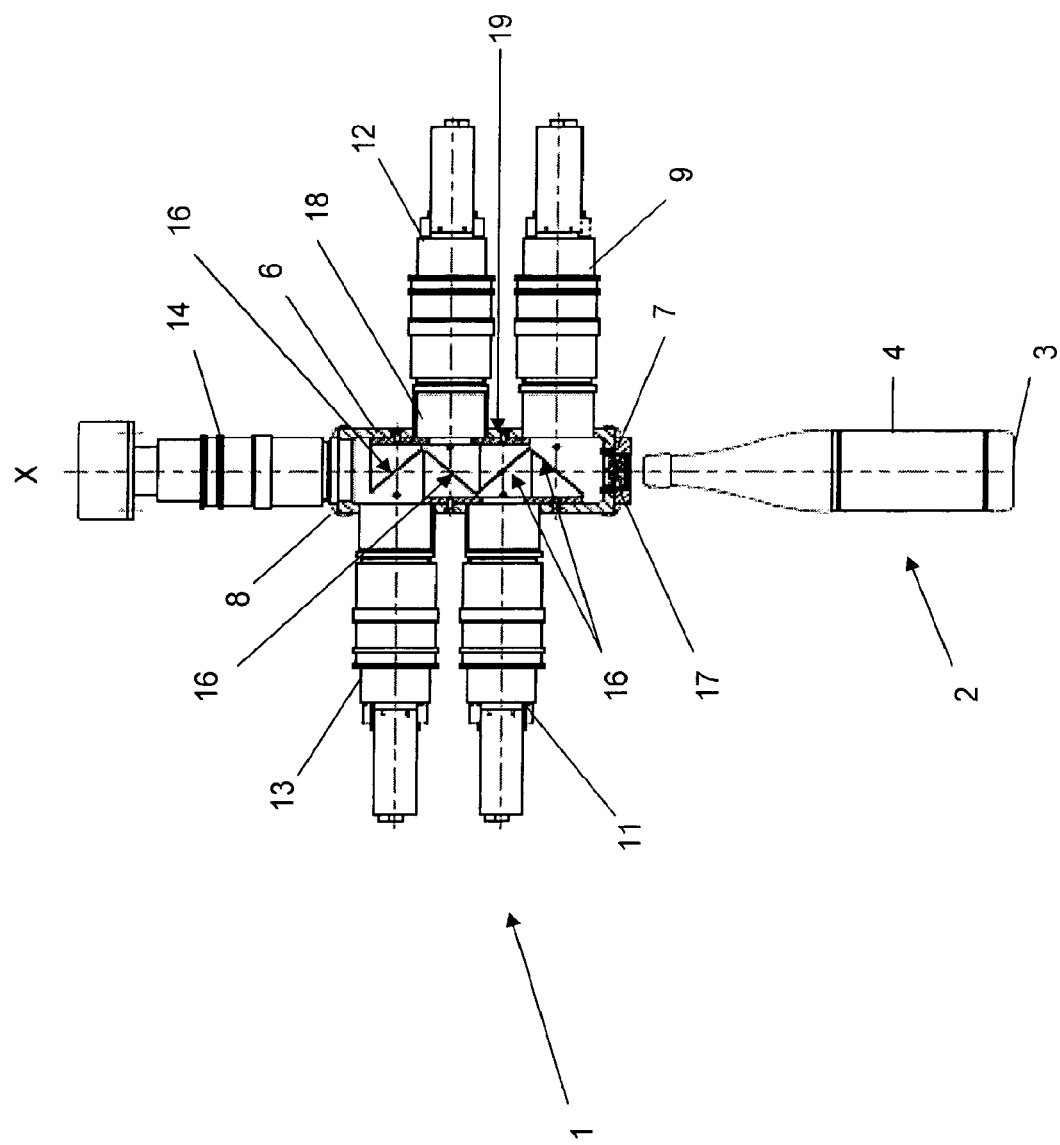

REDUNDANT INSPECTION

CROSS-REFERENCE TO RELATED APPLICATIONS

This application is the National Stage of International Application No. PCT/EP2009/003835, filed on May 29, 2009, which claims the benefit of the Jun. 24, 2008 priority date of German Application Serial No. 10 2008 029 661.9. The contents of both of the foregoing applications are hereby incorporated by reference in their entirety.

FIELD OF INVENTION

The invention relates to an inspection device for checking bottles or similar containers, the inspection device comprising at least one first camera that checks a defined region of the bottle or of a similar container.

BACKGROUND

Bottles or other types of containers can be used for liquids, for example for beverages. These bottles can be produced from a transparent or translucent material, for example glass, or from a translucent plastic material, e.g. PET. While empty, and preferably after having been cleaned, the bottles are moved passed an inspection device.

To permit inspection, an illuminating device is located, for example, below the bottle to be inspected, and a first camera is located opposite the illuminating device. The illuminating device illuminates the bottle so that the camera can check whether there are any foreign substances in the bottle or whether the bottle has sustained damage. Examples of foreign substances include, for example, adhesive films (TESA®) or other unwanted objects and contaminants.

To this end, the camera is aligned onto a bottom region of the bottle such that only the bottom region, or the bottle's bottom, is inspected from the inside. Using a second inspection device, it is possible to inspect an inside wall region of the bottle for unwanted objects, contaminants or damage. If the two inspection devices detect unwanted objects in the bottle, or that the bottle has contaminants or damage in or on the inspected region, the bottle is rejected. Corresponding means are provided for this purpose to process the image acquired by the camera or to compare the image acquired by the camera with another image, and to then transmit a corresponding signal to suitable sorting devices.

Inspecting the interior of the bottle for liquid residue or the like is also known, it being possible to provide a camera that uses infrared light for this purpose. The inspection devices inspect the relevant region (i.e. the bottom and/or inside wall of the bottle), but only once each time. This means that errors can occur and only unreliable assertions concerning the presence of unwanted objects, contaminants in or damage sustained by the inspected region can be made.

In addition, the use of a plurality of inspection devices following one after the other is disadvantageous because a bottle then has to run through a plurality of inspection devices in order to have all of its defined inside regions inspected.

SUMMARY

Consequently, it is an object of the invention to inspect bottles in a cost-effective manner by making a simple improvement to an inspection device of the aforementioned type such that it becomes possible to reliably inspect the defined region of the bottle.

This object is achieved according to the invention by an inspection device in which a first camera is located at an optical channel that has a second camera, the second camera inspecting the same region as the first camera, and wherein, at the optical channel, there is located at a third and fourth camera, that together inspect a further inside region of the bottle.

The invention advantageously makes available a single inspection device that checks the defined region to be inspected at least twice for unwanted objects and contaminants in the interior of the bottle and/or for damage by having a second camera inspect the region inspected by the first camera. In other words, both the first and second cameras are set to independently inspect one and the same region. This means that two images of the defined region to be inspected can be taken and processed, which in turn means that the reliability of the assertions made, for example assertions concerning the presence of unwanted objects in the interior of the bottle and/or the presence of damage, is considerably increased with reference to a one-off inspection.

The two cameras can be located, when viewed in a longitudinal direction of the optical channel, one above the other and to the side of the optical channel. It is also conceivable for the two cameras to be located opposite one another, with reference to a central axis of the optical channel.

The bottom of the bottle can be inspected in a reliable manner by using the two cameras. In a preferred embodiment of the invention, third and fourth cameras are located at the optical channel, with the third and fourth cameras inspecting another defined region of the bottle, for example its side wall. It is also possible for the two cameras to be located to the side of the optical channel one above the other along the longitudinal direction of the optical channel.

In this case any expedient sequence of four cameras is conceivable, for example when viewed in the longitudinal direction, the bottom two cameras located opposite one another at the side inspect the bottom and the other two cameras inspect the side wall of the bottle.

In a further preferred development, it is also possible to locate a camera that processes infrared light at the optical channel, the camera being able to reliably detect, for example, liquid residue in the interior of the bottle.

In order to realize the possible arrangements of five cameras in the preferred manner, one embodiment features an optical channel that, when viewed in longitudinal section, is rectangular and that has optical elements. Naturally it is also possible to select any other suitable geometric arrangement for the optical channel. The optical elements can be realized as beam splitters and optical lenses.

At its inspection end, which is the end oriented towards the bottle, the optical channel preferably has two optical lenses that are located one above the other when viewed in the longitudinal direction. This means that it is possible to inspect both the bottom, using two cameras, and the side wall, using another two cameras, of the bottle using only a single inspection device according to the invention.

The beam splitters are located in the interior of the optical channel. Each camera that is located to the side has an associated beam splitter. Beam splitters, in terms of the invention, are partially transparent optical elements that reflect part of the light incident thereon and that transmit part of the light incident thereon.

In a preferred embodiment, the beam splitters are arranged one above the other in the longitudinal direction. The beam splitters have different transparency values and reflection values so that even the last camera, when viewed in the longitudinal direction, is still able to inspect the interior of the bottle in a reliable manner. For example, when viewed in the longitudinal direction from the inspection end, the first beam splitter has a smaller reflection value and a high transparency value (e.g.: 30% reflected/70% transmitted). When viewed in the longitudinal direction with reference to the inspection end, the last beam splitter has a higher reflection value than the first beam splitter and also a smaller transparency value (e.g.: 60% reflected/40% transmitted). The transparency values and reflection values of the beam splitters located in between are adapted accordingly. In this respect, the beam splitters can also be regarded as transparent mirrors.

The beam splitters are realized such that infrared light is not reflected, as a result of which the beam splitters are completely transparent to infrared light.

In some embodiments, each laterally arranged camera has associated therewith a beam splitter that reflects beams in the direction of that camera such that the relevant inside region of the bottle (i.e. the bottom of the bottle or the side wall of the bottle) can be photographed by that camera.

In other embodiments, each of the laterally arranged cameras has associated therewith an optical lens so that the camera can be adapted to a corresponding optical length, or so that an optical ratio can be set for the camera using the lens. The lenses associated with the cameras can be accommodated in a housing and can be located between the respective cameras and the side wall of the optical channel.

The invention makes available a single inspection device that reliably checks defined regions of the bottle by photographing a region of the bottle twice, once with each of two cameras. The region can be the inside bottom or the inside side wall of the bottle.

An advantage of the apparatus descried herein is that the bottle does not have to be set in rotation because the optical channel, with its optical elements, enables a complete image in the radial direction of the respective region.

Another advantage is that it is possible to operate the two cameras, which in each case inspect the same inside region (bottom/side wall), at different polarizations so that one can be operated in bright field and the other in dark field. This is advantageous because many films are easier to recognize using dark field inspection. Naturally, it is within the terms of the invention to arrange even more than the mentioned five cameras at the optical channel such that more regions than the inside regions described can be inspected.

DESCRIPTION OF THE DRAWING

Further advantageous developments of the invention are disclosed in following description and in the attached FIGURE, which shows an inspection device according to the invention with cameras located at an optical channel.

DETAILED DESCRIPTION

FIG. 1 shows an inspection device 1 for checking bottles 2. Bottles 2 and similar containers are referred to throughout this specification in a general manner as bottles 2.

The bottle 2 has a bottom 3 and a side wall 4. A mouth opening is located opposite the bottom 2. The inspection device 1 checks the interior of the bottle. Preferably, this checking occurs after the bottle has been cleaned. The inspection device 1 checks the interior for unwanted objects, contaminants and/or damage. In this respect, this can be called an empty bottle inspection.

The inspection device 1 includes an illuminating device (not represented). In the exemplary embodiment, the illuminating device is located below the bottle 2, which is conveyed past the illuminating device, for example, in a suspended manner. The illuminating device shines through the bottle 2 from below.

In the exemplary embodiment, the inspection device 1 has an optical channel 6. When viewed in longitudinal section, the optical channel 6 is rectangular with an inspection end 7 and a head end 8 located opposite the inspection end 7.

Four cameras 9, 11, 12, 13 are each located to the side of the optical channel 6. A fifth camera 14 is located at the head end 8. The cameras 9 and 12 as well as 11 and 13, when viewed in the longitudinal direction of the optical channel 6, are located one above the other. With reference to the central axis X of the optical channel 6, two cameras 9 and 12 are located on the right-hand side in the drawing plane and the two other cameras 11 and 13 are located on the left-hand side of the optical channel 6 in the drawing plane.

In each case, two of the four cameras 9 to 13 located to the side together check defined inside regions of the bottle 2. For example, the cameras 9 and 12 check the bottom region and the cameras 11 and 13 check the side walls. Consequently, two photographs of the defined region are taken by one single inspection device 1.

Naturally, the named sequence of the cameras 9 to 13 is purely to be understood as an example. Thus it is possible, within the terms of the invention, for the cameras 9 and 11 or 9 and 13 to inspect the bottom region or the side wall and for the cameras 12 and 13 or 11 and 12 to inspect the other region.

The fifth camera 14 located at the head end checks whether there is any unwanted liquid residue in the bottle 2.

In order to be able to supply the respective cameras 9 to 14 with the desired information, optical elements are located in the optical channel 6. These optical elements are realized as beam splitters 16 or optical lenses 17. The optical channel 6 can also be described as an optical tower on which the five cameras 9 to 14 and the optical elements 16 and 17 are located.

In the illustrated embodiment, two lenses 17, located one above the other in the longitudinal direction, are located at the inspection end 7. At least each of the cameras 9 to 13 located at the side has associated therewith, in each case, a further lens (not represented) and these are each accommodated in a housing 18. The housing 18 is located between a side wall 19 of the optical channel 6 and the respective camera 9 to 13.

In addition, each of the cameras 9 to 13 located to the side has, associated therewith, a beam splitter 16. The beam splitters 16 are realized such that even the last camera, when viewed in the longitudinal direction, can be supplied with information. This means that the beam splitters 16 following one after the other in the longitudinal direction preferably have different transparency or reflection values.

Corresponding openings in the side wall 19 or in the head end 8 are naturally provided in the region of the cameras 9 to 14.

Using the single inspection device 1 according to the invention, it is possibly to carry out a reliable inspection of the interior of the bottle 2. To this end, in each case two cameras are provided. Each such camera inspects the same defined region of the bottle 2. Two further cameras check another defined inside region of the bottle 2. In this respect an inspection device 1 is made available to use for reliably checking inspection regions of the bottle in a reliable manner. The optical channel 6, in this case, is provided in a favorable manner with optical elements such that, in each case, the correlating cameras can be supplied with the corresponding information.

LIST OF REFERENCES

Inspection device
Bottle

Bottom
Side wall of 2
Optical channel
Inspection end
Head end
Camera
Camera
Camera
Camera
Camera
Beam splitter
Optical lens
Housing
Side wall of 6

The invention claimed is:

1. An apparatus for inspecting bottles, said apparatus comprising an optical tower structure, a first camera having a first camera axis, a second camera a second camera axis, a third camera a third camera axis, and a fourth camera a fourth camera axis, wherein said optical tower structure comprises an inspection end, a head end located opposite said inspection end, and a side wall extending between said head end and said inspection end, said side wall defining an enclosure, and a longitudinal axis that extends between said inspection end and said head end, wherein said side wall comprises a first opening for receiving said first camera, wherein said side wall comprises a second opening for receiving said second camera, wherein said side wall comprises a third opening for receiving said third camera, wherein said side wall comprises a fourth opening for receiving said fourth camera, wherein said optical tower structure defines a single optical channel that extends through said enclosure and along said longitudinal axis, wherein said longitudinal axis is collinear with a central axis of said optical channel, wherein said first camera is disposed to be in optical communication with said optical channel through said first opening in said sidewall of said optical tower, wherein said second camera is disposed to be in optical communication with said optical channel through said second opening in said sidewall of said optical tower, wherein said third camera is disposed to be in optical communication with said optical channel through said third opening in said sidewall of said optical tower, wherein said fourth camera is disposed to be in optical communication with said optical channel through said fourth opening in said sidewall of said optical tower, and wherein a first pair of said cameras is configured to inspect a first defined region of said bottle and a second pair of said cameras is configured to inspect a second defined region of said bottle.

2. The apparatus of claim 1, wherein said second camera is disposed above said first camera in a direction defined by said longitudinal axis, wherein said first camera axis is perpendicular to said longitudinal direction, wherein said second camera axis is perpendicular to said longitudinal direction, and wherein said first camera axis and said second camera axis are parallel.

3. The apparatus of claim 1, wherein said first opening in said sidewall and said second opening in said sidewall are disposed on opposite faces of said sidewall, wherein said first camera is disposed through said first opening, wherein said second camera is disposed through said second opening, wherein said first camera and said second cameras are disposed on opposite faces of said side wall, wherein said first camera axis is perpendicular to said longitudinal direction, and wherein said second camera axis is perpendicular to said longitudinal direction.

4. The apparatus of claim 3, wherein said first camera is closer to said head end than said second camera, and wherein said second camera is closer to said inspection end than said first camera.

5. The apparatus of claim 1, further comprising a fifth camera having a fifth camera axis, wherein said fifth camera is disposed at said head end, wherein said fifth camera axis is collinear with said central axis, wherein said fifth camera axis is perpendicular to said first camera axis, wherein said fifth camera axis is perpendicular to said second camera axis, wherein said fifth camera axis is perpendicular to said third camera axis, and wherein said fifth camera axis is perpendicular to said fourth camera axis.

6. The apparatus of claim 5, wherein said fifth camera is an infrared camera.

7. The apparatus of claim 1, wherein a longitudinal section of said optical channel is rectangular.

8. The apparatus of claim 1, wherein said optical tower structure comprises optical elements disposed therein.

9. The apparatus of claim 8, wherein said optical elements comprise beam splitters.

10. The apparatus of claim 9, wherein said beam splitters comprise a first beam splitter disposed within said optical channel, and a second beam splitter disposed within said optical channel, wherein said first beam splitter is disposed to direct a first portion of a beam that is parallel to said central axis to said first camera along said first camera axis and to allow transmission of a second portion of said beam toward said second beam splitter, and wherein said second beam splitter is disposed to direct a first portion of said second portion of said beam to said second camera along said second camera axis and to allow transmission of a second portion of said second portion of said beam in a direction along said central axis of said optical channel.

11. The apparatus of claim 10, wherein said first beam splitter has a first transparency, and a second beam splitter has a second transparency, wherein said first transparency is different from said second transparency, whereby a ratio of said first portion of said beam to said second portion of said beam is different from a ratio of said first portion of said second portion of said beam and said second portion of said second portion of said beam, said difference being a function of a difference between said first transparency and said second transparency.

12. The apparatus of claim 8, wherein said optical elements comprise an optical lens disposed at said inspection end.

13. The apparatus of claim 8, wherein said optical elements comprise a first optical lens at said inspection end, and a second optical lens at said inspection end, wherein said first optical lens is displaced along said central axis, whereby said first optical lens is closer to said head end than said second optical lens.

14. The apparatus of claim 1, further comprising a first optical lens and a second optical lens, wherein said first optical lens is disposed such that said first camera axis intersects said first optical lens, and wherein said second optical lens is disposed such that said second camera axis intersects said second optical lens, whereby said first optical lens is associated with said first camera and said second optical lens is associated with said second camera.

* * * * *